United States Patent
Sharma (10) Patent No.: US 9,656,068 B2
(45) Date of Patent: *May 23, 2017

(54) METHOD AND APPARATUS FOR STIMULATING THE VASCULAR SYSTEM

(71) Applicant: Virender K. Sharma, Paradise Valley, AZ (US)

(72) Inventor: Virender K. Sharma, Paradise Valley, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/728,630

(22) Filed: Jun. 2, 2015

(65) Prior Publication Data

US 2016/0101283 A1    Apr. 14, 2016

Related U.S. Application Data

(63) Continuation of application No. 12/575,713, filed on Oct. 8, 2009, now Pat. No. 9,079,028.

(60) Provisional application No. 61/104,054, filed on Oct. 9, 2008.

(51) Int. Cl.
*A61N 1/36* (2006.01)
*A61N 1/05* (2006.01)

(52) U.S. Cl.
CPC ....... *A61N 1/36007* (2013.01); *A61N 1/0509* (2013.01); *A61N 1/36* (2013.01); *A61N 1/36114* (2013.01); *A61N 1/36117* (2013.01)

(58) Field of Classification Search
CPC .............................. A61N 1/36; A61N 1/36007
See application file for complete search history.

(56) References Cited

U.S. PATENT DOCUMENTS

| | | | |
|---|---|---|---|
| 8,024,035 B2 | 9/2011 | Dobak | |
| 9,079,028 B2* | 7/2015 | Sharma | A61N 1/36007 |
| 2002/0016615 A1 | 2/2002 | Dev | |
| 2004/0044376 A1 | 3/2004 | Flesler | |
| 2004/0236382 A1* | 11/2004 | Dinsmoor | A61N 1/05 607/40 |
| 2006/0074449 A1 | 4/2006 | Denker | |
| 2006/0161217 A1 | 7/2006 | Jaax | |
| 2006/0287678 A1* | 12/2006 | Shafer | A61N 1/36071 607/2 |
| 2007/0162085 A1* | 7/2007 | DiLorenzo | A61N 1/36007 607/40 |
| 2007/0276293 A1 | 11/2007 | Gertner | |

(Continued)

FOREIGN PATENT DOCUMENTS

WO    2010042686    4/2010

OTHER PUBLICATIONS

International Search Report for PCT/US2009/059947, Feb. 12, 2010.

*Primary Examiner* — Catherine Voorhees
(74) *Attorney, Agent, or Firm* — Novel IP (57) ABSTRACT

The present invention provides methods of treating a gastrointestinal condition. In some embodiments, the method generally includes administering a chemical or electrical stimulus to an artery of the gastrointestinal vasculature of the subject, a vein of the gastrointestinal vasculature of the subject, a nerve supplying an artery of the gastrointestinal vasculature of the subject, and/or a nerve supplying a vein of the gastrointestinal vasculature of the subject, wherein the chemical or electrical stimulus is effective for treating a gastrointestinal condition.

14 Claims, 6 Drawing Sheets

(56) References Cited

U.S. PATENT DOCUMENTS

| | | |
|---|---|---|
| 2009/0192570 A1 | 7/2009 | Jaax |
| 2012/0150245 A1* | 6/2012 | Rezai ................ A61N 1/36007 607/3 |
| 2013/0238066 A1* | 9/2013 | Boggs, II ............ A61N 1/0558 607/116 |

* cited by examiner

52=microprocessor
55= 2nd device
56= 1st device
57= 2nd reservoir
58= 1st reservoir

FIG. 6

METHOD AND APPARATUS FOR STIMULATING THE VASCULAR SYSTEM

CROSS-REFERENCE

The present application is a continuation application of U.S. patent application Ser. No. 12/575,713, entitled "Method and Apparatus for Stimulating the Vascular System" and filed on Oct. 8, 2009, which relies on U.S. Provisional Patent Application No. 61/104,054, of the same title and filed on Oct. 9, 2008, for priority, both of which are incorporated herein by reference in their entirety.

FIELD

The present invention is directed to the field of obesity management and, more specifically, to stimulating the vascular system of a patient in order to encourage weight loss by the patient.

BACKGROUND

Obesity is a common condition and a major public health problem in developed nations including the United States of America. Today, 64.5% of American adults, about 127 million people, are either overweight or obese. Data suggest that 300,000 Americans die prematurely from obesity-related complications each year. Many children are overweight or obese in the United States; hence, the steady increase in the number of overweight Americans is expected to continue. It has been estimated that obesity costs the United States approximately $100 billion annually in direct and indirect health care expenses and in lost productivity. This trend is also apparent in many other developed countries.

Morbid obesity is defined as possessing either a body weight more than 100 pounds greater than normal or a body mass index (BMI) greater than 40 kg/m$^2$. Approximately 5% of the U.S. population meets at least one of these definitions. A BMI greater than 30 kg/m$^2$ is associated with significant co-morbidities. Morbid obesity is associated with many diseases and disorders including, for example, diabetes, hypertension, heart attacks, strokes, dyslipidemia, sleep apnea, Pickwickian Syndrome, asthma, lower back and disc disease, weight-bearing osteo-arthritis of the hips, knees, ankles and feet, thrombophlebitis and pulmonary emboli, intertriginous dermatitis, urinary stress incontinence, gastroesophageal reflux disease (GERD), gallstones, and sclerosis and carcinoma of the liver. In women, infertility, cancer of the uterus, and cancer of the breast are also associated with morbid obesity. Taken together, the diseases associated with morbid obesity markedly reduce the odds of attaining an average lifespan and raise annual mortality in affected people by a factor of 10 or more.

Current treatments for obesity include diet, exercise, behavioral treatments, medications, surgery (open and laproscopic) and endoscopic devices. Also, additional treatments for obesity are currently being evaluated in clinical trials. However, a high efficacy pharmaceutical treatment has not yet been developed. Further, short-term and long-term side effects of pharmaceutical treatments may concern consumers, pharmaceutical providers, and/or their insurers. Generally, diet or drug therapy programs have been disappointing and fail to bring about significant, sustained weight loss in the majority of morbidly obese people.

Currently, most morbid obesity operations are, or include, gastric restrictive procedures, involving the creation of a small (e.g., 15-35 mL) upper gastric pouch that drains through a small outlet (e.g., 0.75-1.2 cm), setting in motion the body's satiety mechanism. About 15% of morbid obesity operations done in the United States involve gastric restrictive surgery combined with a malabsorptive procedure. Typical malabsorptive procedures divide small intestinal flow into a biliary-pancreatic conduit and a food conduit. Potential long-term problems with surgical procedures, including those seen after any abdominal procedure, are notorious and can include, for example, ventral hernia and small bowel obstruction. In addition, long-term problems specific to bariatric procedures can include, for example, gastric outlet obstruction, marginal ulceration, protein malnutrition, and vitamin deficiency.

Other surgical strategies for treating obesity include endoscopic procedures, many of which are still in development. Endoscopically placed gastric balloons restrict gastric volume and result in satiety with smaller meals. Endoscopic procedures and devices to produce gastric pouch and gastrojejunal anastomosis to replicate laparoscopic procedures are also in development. These procedures, however, are not without risks.

Gastric electric stimulation (GES) and vagal stimulation (BBLOC) are other procedures currently in clinical trials. Both GES and VBLOC employ an implantable, pacemaker-like device to deliver low-level electrical stimulation to the stomach (GES) or vagus nerve (VBLOC). The procedures involve a surgeon suturing electrical leads to the outer lining of the stomach wall in GES vagus nerve in VBLOC. The leads are then connected to a device that may be implanted in the patient, for example, just under the skin in the abdomen. An external programmer may communicate a prescribed level of electrical stimulation appropriate for the patient. The TRANSCEND (Medtronic Transneuronix Inc., Mount Arlington, N.J.) implantable gastric stimulation device for GES is currently being evaluated for the treatment of obesity. The MAESTRO RF2 System (EnteroMedics, Inc., St. Paul, Minn.), an implantable vagal stimulation device for VBLOC, is currently in U.S. trials for the treatment of obesity. Exemplary treatments and treatment systems can be found in U.S. patent application Ser. No. 12/359,317, filed on Jan. 25, 2009, Ser. No. 11/539,645, filed on Oct. 9, 2006, and Ser. No. 12/030,222, filed on Feb. 13, 2008, PCT Patent Application No. PCT/US08/56479, and U.S. Pat. No. 6,901,295, which are incorporated herein by reference.

U.S. Pat. No. 6,993,391 discloses an apparatus that "comprises a control unit 190, and one or more electrodes 200 applied to or in a vicinity of respective sites of the arterial supply 130 of the patient's small intestine 120. If appropriate, some or all of electrodes 200 may be placed on the superior mesenteric artery 110, or in a vicinity thereof. Typically, control unit 190 drives electrodes 200 to apply signals which cause a controllable level of constriction of the arteries to which these electrodes are coupled. Alternatively or additionally, other transducers (not shown) are implanted in the patient in a vicinity of arterial supply 130, and are driven by control unit 190 to induce some or all of the arteries in supply 130 to contract. As appropriate, these transducers may induce this contraction using mechanical or chemical means. The constriction produced by apparatus 118 preferably transiently and controllably reduces the blood flow to small intestine 120, and thereby reduces the total number of calories which are ultimately absorbed into the patient's bloodstream during and after eating a meal." However, this treatment method only targets the superior mesenteric artery (SMA) which is the arterial supply of small intestine in order to cause malabsorption, which has limited efficacy and does not curtail appetite or induce satiety and hence does not decrease caloric intake. In addition, efficacy of stimulating only SMA may decrease over time due to development of collateral blood supply from other arteries of gastrointestinal vasculature.

SUMMARY

It has been discovered that restricting blood flow to at least a portion of the gastrointestinal tract can be useful to curb one's appetite, induce feelings of satiety, and, therefore, be useful as treatment for certain conditions of the gastrointestinal tract such as, for example, obesity.

Consequently, in one aspect, the present invention provides a method of treating a gastrointestinal condition in a subject. Generally, the method includes providing an apparatus comprising at least one electrode operably connected to a stimulus generator, placing the at least one electrode in electrical communication with a target comprising one or more of the following: an artery of the gastrointestinal vasculature of the subject, a vein of the gastrointestinal vasculature of the subject, a nerve supplying an artery of the gastrointestinal vasculature of the subject, and a nerve supplying a vein of the gastrointestinal vasculature of the subject, and causing the stimulus generator to generate an electrical stimulus administered to the target through the at least one electrode, wherein the electrical stimulus is effective for treating a gastrointestinal condition.

In some embodiments, the apparatus can further include a radio-frequency (RF) receiver operably connected to the stimulus generator and a RF transmitter in operable communication with the RF receiver; and the method can include sending a signal from the RF transmitter to the RF receiver, which results in the stimulus generator generating an electrical stimulus.

In some embodiments, the apparatus can further include a microprocessor operably connected to the stimulus generator, wherein at least one parameter of the stimulus is controlled by the microprocessor, wherein the parameter is selected from the group consisting of: the amplitude, frequency, pattern, period, and duration of the stimulation, and wherein causing the stimulus generator to generate an electrical stimulus administered to the target through the at least one electrode comprises the microprocessor sending a signal to the stimulus generator signaling the stimulus generator to generate a stimulus.

In some embodiments, the apparatus can further include at least one sensing electrode operably connected to the signal generator and in communication with at least a portion of the subject's gastrointestinal tract, wherein the at least one sensing electrode senses at least one physiological stimulus resulting from the subject feeling hungry or ingesting food, and wherein the at least one sensing electrode transmits a signal to the signal generator to administer an electrical signal to the target after sensing the at least one physiological stimulus resulting from the subject ingesting food.

In some embodiments, the signal administered to the target may be a chemical signal rather than an electrical signal. In such embodiments, the method generally includes providing an apparatus comprising at least one infusion catheter operably connected to a pump, placing the at least one infusion catheter in chemical communication with a target comprising one or more of the following: an artery of the gastrointestinal vasculature of the subject, a vein of the gastrointestinal vasculature of the subject, a nerve supplying an artery of the gastrointestinal vasculature of the subject, and a nerve supplying a vein of the gastrointestinal vasculature of the subject, and causing the pump to administer a chemical stimulus to the target through the at least one infusion catheter, wherein the chemical stimulus is effective for treating a gastrointestinal condition.

In some embodiments, the apparatus can further include a RF receiver operably connected to the pump and a RF transmitter in operable communication with the RF receiver, and the method can further include sending a signal from the RF transmitter to the RF receiver, which results in the pump administering a chemical stimulus.

In some embodiments, the apparatus can further include a microprocessor operably connected to the pump, wherein at least one parameter of the stimulus is controlled by the microprocessor, wherein the parameter is selected from the group consisting of: the volume, frequency, pattern, period, and duration of the stimulation, and wherein causing the pump to administer a chemical stimulus to the target through the at least one infusion catheter comprises the microprocessor sending a signal to the pump signaling the pump to administer the chemical stimulus.

In still other embodiments, the apparatus can further include at least one sensing electrode operably connected to the pump and in communication with at least a portion of the subject's gastrointestinal tract, wherein the at least one sensing electrode senses at least one physiological stimulus resulting from the subject feeling hungry or ingesting food, and wherein the at least one sensing electrode transmits a signal to the pump to administer a chemical signal to the target after sensing the at least one physiological stimulus resulting from the subject ingesting food.

The above summary of the present invention is not intended to describe each disclosed embodiment or every implementation of the present invention. The description that follows more particularly exemplifies illustrative embodiments. However, embodiments other than those expressly described are possible and may be made, used, and/or practiced under circumstances and/or conditions that are the same or different from the circumstances and/or conditions described in connection with the illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

The present invention provides methods of treating a gastrointestinal (GI) disorder. Very generally, the treatment involves controlling the function of the gastrointestinal system by regulating the blood flow through the tissues and organs of the gastrointestinal tract. Generally, the control of blood flow through the GI tract is accomplished by administering a stimulus to either the vessels that supply blood to the GI tract or nerves that control those blood vessels.

Definitions

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribe treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Mesenteric blood supply is important for proper functioning of the gastrointestinal system and is important for the digestion of all nutrients. Interrupting the mesenteric vascular supply may impair digestion of various nutrients, including fat digestion, and therefore can be helpful in managing conditions of ove-nutrition including, fobr example, obesity.

Figure 1:
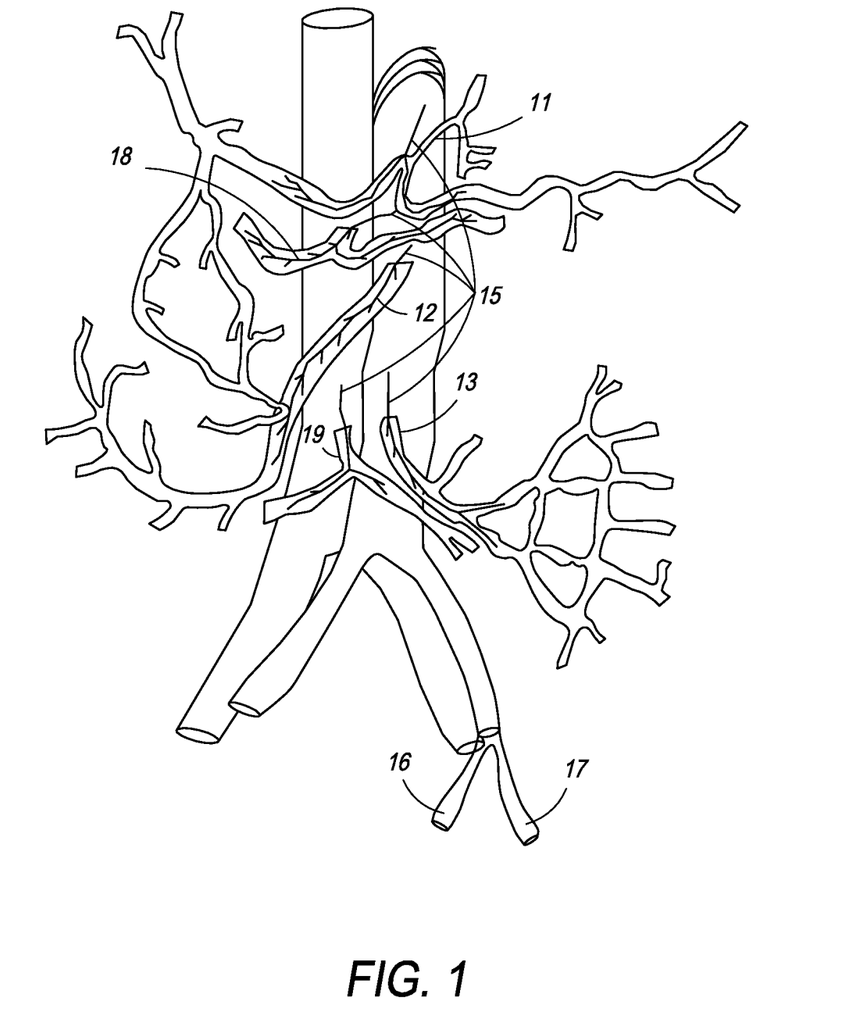
FIG. 1 is a schematic illustration of a portion of the mesenteric vascular system.

Referring now to the various views of the accompanying drawings, FIG. 1 illustrates a portion of the gastro-intestinal (GI) tract including a celiac artery 11, a superior mesenteric artery 12, an inferior mesenteric artery 13, an internal iliac artery 16, an external iliac artery 17, a superior mesenteric vein 18, and an inferior mesenteric vein 19. As used herein, the term "mesenteric arteries" refers collectively to the celiac artery 11, superior mesenteric artery 12 and an inferior mesenteric artery 13. Also, the term "mesenteric veins" refers collectively to the superior mesenteric vein 18 and inferior mesenteric vein 19.

The mesenteric arteries constitute the major arterial blood supply of the gastrointestinal system and the mesenteric veins constitute the major system draining the blood from the gastrointestinal system. The flow of the blood to and from the gastrointestinal system is controlled by the tonic contraction and relaxation of the smooth muscle in the blood vessels of the mesenteric vascular system. The blood flow in the fasting state maintains the viability of the gastrointestinal tract. In the fed state, the work of the gastrointestinal tract increases and requires a corresponding increased need for oxygen and nutrients to the gastrointestinal system. The increased need for oxygen and nutrients is met by increasing the supply of blood to the gastrointestinal tract, accomplished by dilating the mesenteric arteries. This phenomenon of increasing the energy requirement of the gastrointestinal tract after a eating is known as the specific dynamic action of food. In situations of dehydration or hemorrhage, blood is shunted away from the gastrointestinal tract to other vital organs. This decrease in blood supply to the gastrointestinal tract is accomplished by the constriction of the mesenteric arteries. Subjects having a blockage in the mesenteric arteries due to, for example, atherosclerotic artery disease can have difficulty increasing the blood supply to the gastrointestinal tract that is required to process and digest food after a meal. These subjects can develop pain, loss of appetite, and weight loss.

The methods described herein involve controlling a subject's appetite, inducing satiety, and/or inducing weight loss by regulating the blood flow to the intestinal tract and more specifically by regulating the specific dynamic action of food—i.e., the meal-induced increase in the blood supply to the gastrointestinal tract—through stimulation of the mesenteric vasculature and/or nerves supplying the mesenteric vasculature.

The methods described herein can also be applied to treating certain cardiovascular conditions or indications, including angina, chest tightening, unstable angina, stable angina, coronary artery disease, atherosclerotic disease, heart failure or myocardial infarction. By reducing the blood flow to the intestinal tract and more specifically by minimizing the increase of blood flow to the gastrointestinal tract due to the specific dynamic action of food, the present invention can also help treat the aforementioned cardiovascular conditions.

In order to reduce the meal-induced blood flow to the gastrointestinal tract, an electrical, chemical, or mechanical stimulus effective for treating a gastrointestinal condition is applied to one or more target locations in the celiac artery 11, superior mesenteric artery 12, inferior mesenteric artery 13, internal iliac artery 16, external iliac artery 17, superior mesenteric vein 18, or inferior mesenteric vein 19, or the nerves 15 supplying the celiac artery 11, superior mesenteric artery 12, inferior mesenteric artery 13, internal iliac artery 16, external iliac artery 17, superior mesenteric vein 18, or inferior mesenteric vein 19. As used herein, a stimulus "effective for treating a gastrointestinal condition" includes stimulation sufficient to result in, for example, contraction of at least one or more of the celiac artery 11, superior mesenteric artery 12, inferior mesenteric artery 13, internal mesenteric artery 16, external iliac artery 17, superior mesenteric vein 18, or inferior mesenteric vein 19, thus reducing the flow of blood into the gastrointestinal tract.

A reduction in the blood flow to the gastrointestinal tract can interrupt gastrointestinal function such as, for example, digestion and absorption of nutrients such as, for example, fat. The stimulation may result in curbing a subject's appetite and/or inducing satiety, anorexia, and/or weight loss in a subject due to discomfort incurred by a patient upon ingestion and, accordingly, stimulation of the target locations. Thus, in certain embodiments, a stimulus "effective for treating a gastrointestinal condition" can include stimulation that may, for example, curb a subject's appetite and/or induce satiety, anorexia, and/or weight loss in a subject. In other embodiments, a stimulus "effective for treating a gastrointestinal condition" can include a stimulus effective for treating a condition secondary to obesity such as, for example, diabetes, hypertension, heart attack, stroke, dyslipidemia, sleep apnea, Pickwickian Syndrome, asthma, lower back and disc disease, weight-bearing osteo-arthritis of the hips, knees, ankles and feet, thrombophlebitis and pulmonary emboli, intertriginous dermatitis, urinary stress incontinence, gastroesophageal reflux disease (GERD), gallstones, sclerosis, carcinoma of the liver, infertility, cancer of the uterus, and/or cancer of the breast.

In one embodiment, at least one electrode set is placed in the mesenteric circulation near one or more of the celiac artery 11, superior mesenteric artery 12, inferior mesenteric artery 13, internal iliac artery 16, external iliac artery 17, superior mesenteric vein 18 or inferior mesenteric vein 19 or a branch of the celiac artery 11, superior mesenteric artery 12, inferior mesenteric artery 13, internal iliac artery 16, external iliac artery 17, superior mesenteric vein 18 or inferior mesenteric vein 19. Each electrode set includes at least one active electrode and at least one ground electrode. The electrode set may be arranged in any pattern that produces the desired stimulation to the celiac artery 11, superior mesenteric artery 12, inferior mesenteric artery 13, internal iliac artery 16, external iliac artery 17, superior mesenteric vein 18 or inferior mesenteric vein 19, or a branch of the celiac artery 11, superior mesenteric artery 12, inferior mesenteric artery 13, internal iliac artery 16, external iliac artery 17, superior mesenteric vein 18 or inferior mesenteric vein 19 such as a circumferential pattern, along a longitudinal axis, an irregular pattern, or other placement.

In a preferred embodiment, the celiac artery or a branch of a celiac artery is stimulated by itself or in combination with at least one other vascular structure. In another preferred embodiment, the celiac artery or a branch of a celiac artery is stimulated in combination with the SMA or a branch of SMA. In yet another preferred embodiment, at least two vascular structures, such as arteries, veins, or nerves associated with the arteries or veins, are stimulated concurrently or in a predefined sequence, or a combination of both. The predefined sequence can be in rapid or slow succession.

Figure 2:
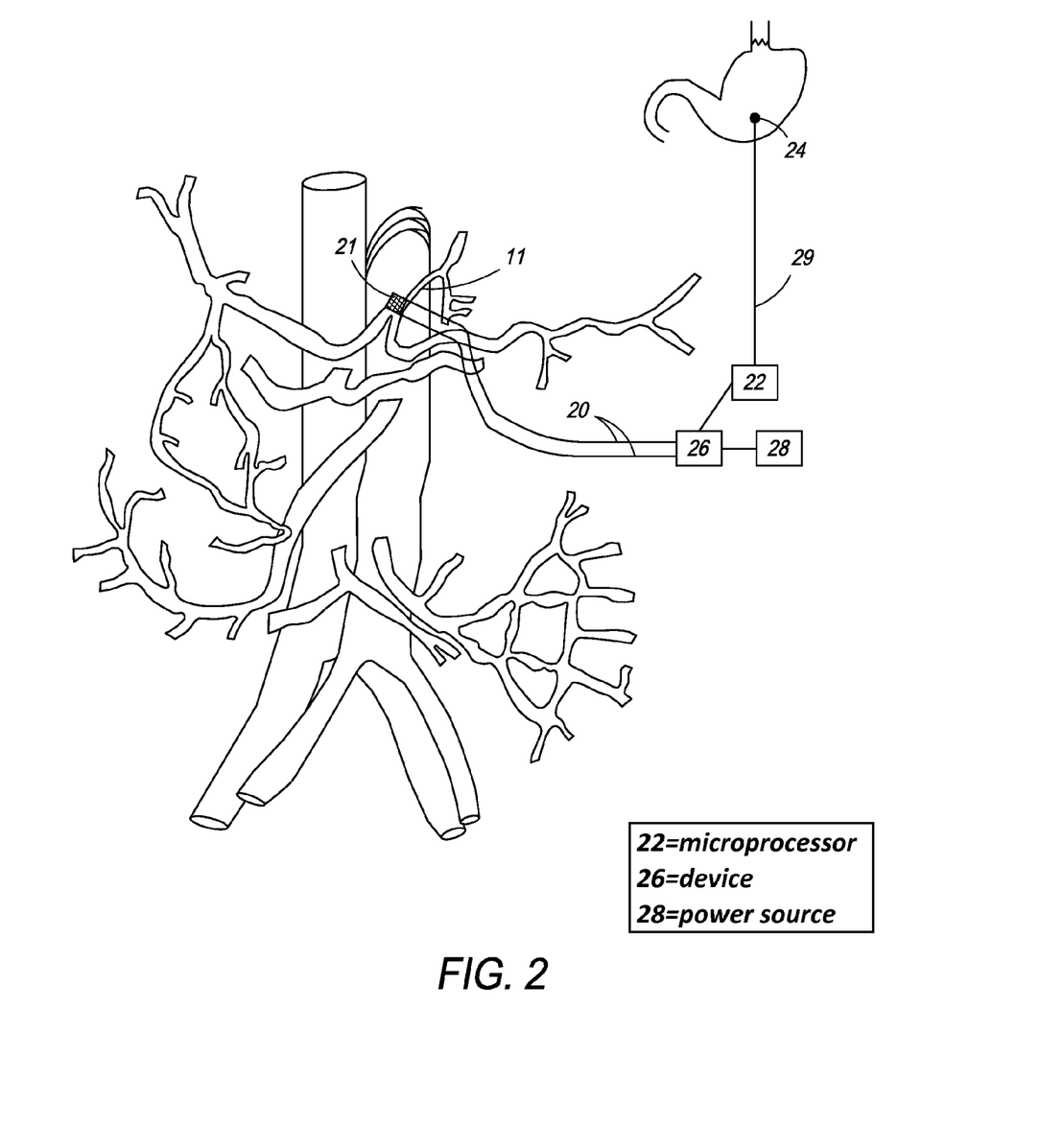
FIG. 2 is a schematic illustration of an exemplary electrode set implanted in the celiac artery.

FIG. 2 illustrates one embodiment where electrode set 21 is placed in a loose linear configuration in the celiac artery 11. A device comprising a pulse generator 26 transmits a signal that causes the electrode set 21 to deliver an electrical stimulation to the celiac artery 11. The device 26 is connected to a power source 28 for supplying a source of power. The device 26 is further connected to the electrode set 21 by wires 20 for transmitting an electrical stimulus signal to the electrode set 21. Alternatively, the electrode set 21 may be coupled to the device 26 in a wireless fashion using a radio frequency (RF) link, an ultrasonic link, a thermal link, a magnetic link, an electromagnetic link, or an optical link. Stimulation of the celiac artery 11 through the electrode set 21 can induce vasoconstriction of the celiac artery 11, which in turn can reduce blood supply to the upper gastrointestinal tract. The devices and control systems disclosed in U.S. patent application Ser. No. 12/359,317, filed on Jan. 25, 2009, which is incorporated herein by reference in its entirety, can be used for all embodiments of the inventions disclosed in this application.

In some embodiments, the stimulator device 26 could be triggered manually by, for example, a medical professional, a caregiver, or the subject. Alternatively, a set of sensing electrodes 24 can detect one of the physiological parameters associated with eating a meal and generate a signal to deliver an electrical stimulus to the celiac artery 11, which can result in meal-induced celiac vasoconstriction, thereby curbing a sbject's appetite and/or inducing anorexia, satiety, and/or weight loss in the subject. Exemplary physiological parameters are identified below.

Figure 3:
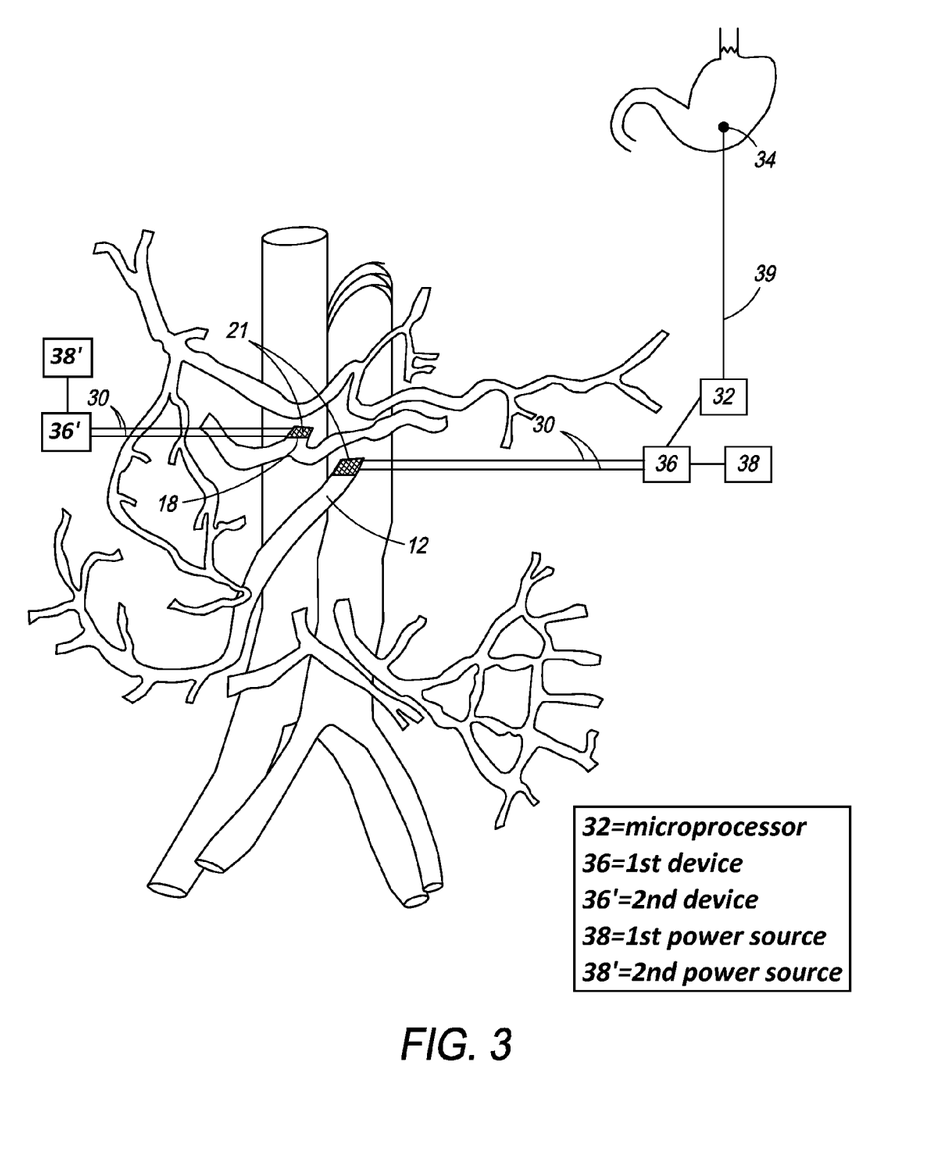
FIG. 3 is a schematic illustration of an exemplary electrode set implanted in the superior mesenteric vessels.

FIG. 3 shows another embodiment in which the electrode set 21 is placed on one of the superior mesenteric artery 12 or superior mesenteric vein 18. First and second devices comprising a pulse generator 36, 36' are connected to first and second power sources 38, 38' for supplying a source of power. The devices 36, 36' are further connected to the electrode sets 21 by wires 30, as previously described. Alternatively, the electrode sets 21 may be coupled to the device 36, 36' in a wireless fashion, as previously described. The stimulating electrode 21 can stimulate the superior mesenteric artery 12 to cause superior mesenteric artery 12 vasoconstriction or stimulate the superior mesenteric vein 18 to cause superior mesenteric vein 18 vasoconstriction, thereby decreasing blood supply to middle part of the gastrointestinal system.

In some embodiments, the stimulator devices 36, 36' can be triggered manually by, for example, a medical professional, a caregiver, or the subject. Alternatively, a set of sensing electrodes 34 can detect one of the physiological parameters associated with a meal and generate a signal to cause superior mesenteric artery 12 or superior mesenteric vein 18 vasoconstriction, and decrease blood supply to middle part of the gastrointestinal system. This can induce feelings of fullness, satiety and/or reduced appetite.

Figure 4:
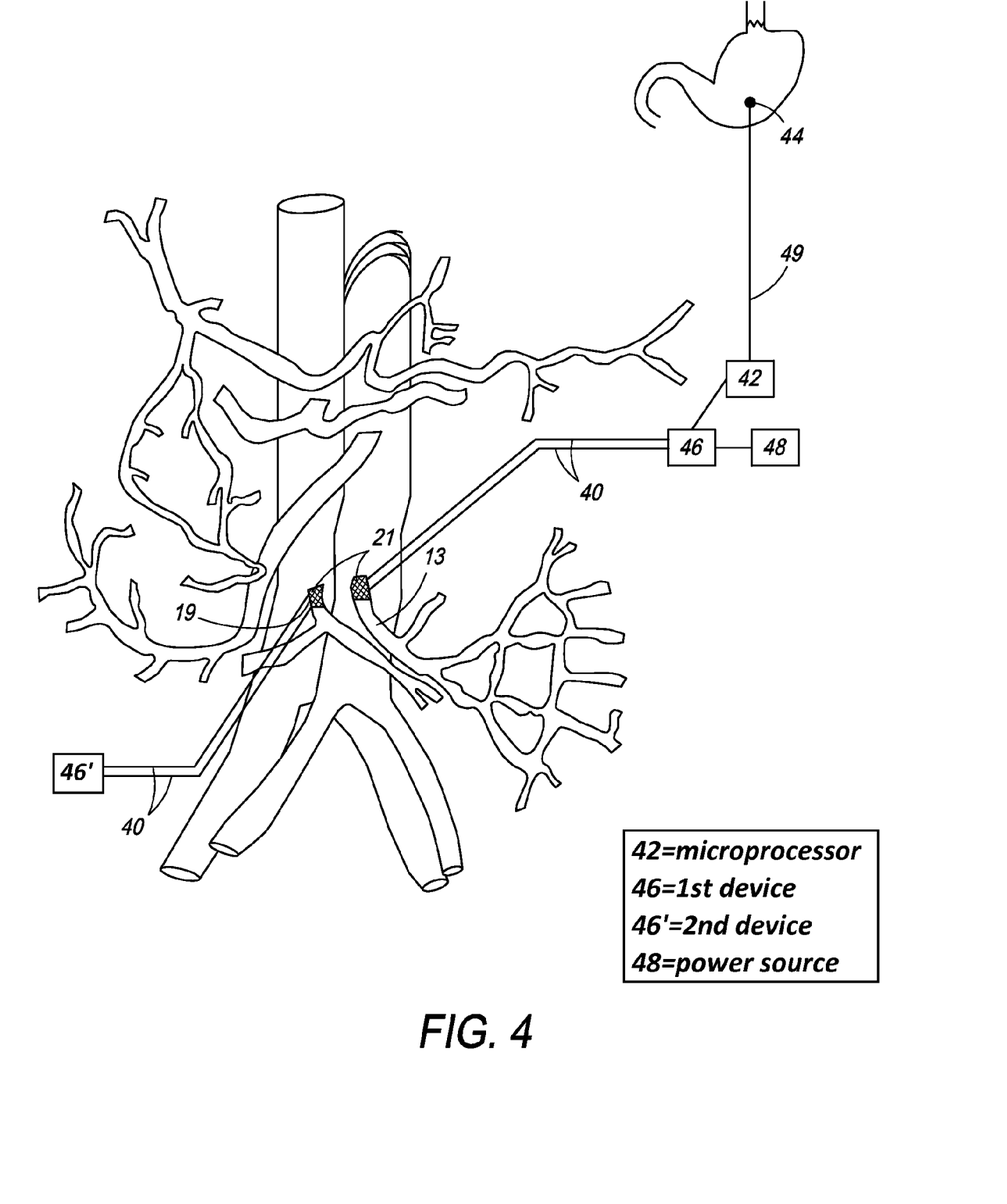
FIG. 4 is a schematic illustration of an exemplary electrode set implanted in the inferior mesenteric vessels.

FIG. 4 shows another embodiment in which the electrode set 21 is placed in one of the inferior mesenteric artery 13 or inferior mesenteric vein 19. A first device comprising a pulse generator 46 is connected to a power source 48 for supplying a source of power. The devices 46, 46' may be further connected to the electrode set 21 by wires 40, as previously described. Alternatively, the electrode set 21 may be coupled to the devices 46, 46' in a wireless fashion. One of the devices 46, 46' may control one electrode set 21. Alternatively, one of the devices 46, 46' may control more than one electrode set. The stimulating electrode 21 can stimulate the inferior mesenteric artery 13 or inferior mesenteric vein 19 causing vasoconstriction, and decrease blood supply to lower gastrointestinal system.

In some embodiments, the stimulator device 46, 46' can be triggered manually by, for example, a medical professional, a caregiver, or the subject. Alternatively, a set of sensing electrodes 44 can detect one of the physiological parameters associated with a meal and generate a signal to cause the delivery of an electrical stimulus which can cause inferior mesenteric artery 13 or inferior mesenteric vein 19 vasoconstriction, and decrease blood supply to the lower gastrointestinal system.

In each embodiment described above, the decrease in blood supply to the gastrointestinal (GI) system—whether to the upper GI system as depicted, for example, in FIG. 2, the middle GI system as depicted, for example, in FIG. 3, or the lower GI system as depicted, for example, in FIG. 4—can curb a subjects appetite and/or induce anorexia, satiety, and/or weight loss in the subject. In one embodiment, a subject's appetite is considered curbed or satiety is induced if, relative to a patient's historical average daily, weekly, monthly, quarterly, or yearly caloric intake, the patient is ingesting 5% or more (e.g. 10%, 20%, 30%, 40%, 50%, 60%, 70%, and on) fewer calories. In another embodiment, a subject's appetite is considered curbed or satiety is induced if, relative to a patient's historical average daily, weekly, monthly, quarterly, or yearly caloric intake, the patient is ingesting less than a threshold number of maximum calories, wherein the threshold number of maximum calories is defined based upon a patient's desired weight loss goal. In another embodiment, a subject incurs substantial weight loss if a subject has lost at least 30% of the subject's excess weight (calculated by subtracting a target weight from the subject's current weight). In another embodiment, a subject incurs substantial weight loss if a subject has lost at least 10% or more of the subject's excess weight (calculated by subtracting a target weight from the subject's current weight).

Also in each embodiment, the electrode set 21 can provide an electrical stimulus of from about 1 microampere (µAmp) up to about 100 Amp, although the methods described herein may be practiced by providing an electrical stimulation outside of this range. Typically, the amplitude of the electrical stimulus can be from about 1 milliAmp (mAmp) to about 10 Amp. In some embodiments, the electrical stimulus can be less than about 10 amp such as, for example, less than 1 amp. In certain embodiments, the amplitude of the electrical stimulus can be from about 5 mAmp to about 100 mAmp such as, for example, 10 mAmp. Also, certain treatments may include multiple electrical stimuli having any combination of varying amplitudes.

An electrical stimulus "dose" can be provided continuously or intermittently. For example, an electrical stimulus may be provided one time, may be provided continuously for a prescribed period, or may be provided in a series of intermittent stimuli over a prescribed period. The prescribed period may be such as, for example, from about 1 millisecond (msec) to about one hour. Intermittent electrical stimuli may be provided at regular, prescribed intervals within the treatment period. For example, intermittent electrical stimuli, one second in length, may be provided for, for example, one hour. In other cases, intermittent electrical stimuli may be provided on an "as needed" basis. Also, certain treatments may include multiple electrical stimuli provided over any combination of varying treatment periods.

An electrical stimulus may have any pattern necessary to produce the desired result, including a square, rectangular, sinusoidal, or saw-tooth shape. Also, certain treatments may include multiple electrical stimuli including any combination of patterns.

The frequency of the electrical stimulus can be in the range of approximately 1 microHertz (µHz) to about 1 megaHertz (MHz), although the methods described herein may be practiced by administering electrical stimuli having a frequency outside of this range. Typically, an electrical stimulus may have a frequency of about 1 mHz to about 1 MHz such as, for example, a frequency of from about 0.1 Hz to about 10 Hz. In certain embodiments, an electrical stimulus may be administered at a frequency of about 1 Hz. Also, certain treatments may include multiple electrical stimuli including any combination of frequencies.

Electrodes of the electrode set 21 can be placed in the tunica intima, tunica media, tunica externa and/or adventitia of the celiac artery 11, superior mesenteric artery 12, inferior mesenteric artery 13, internal iliac artery 16, external iliac artery 17, superior mesenteric vein 18, and/or inferior mesenteric vein 19. Alternatively, electrodes of the electrode set 21 may be placed on nerves 15 supplying the celiac artery 11, superior mesenteric artery 12, inferior mesenteric artery 13, internal iliac artery 16, external iliac artery 17, superior mesenteric vein 18, and/or inferior mesenteric vein 19 or a branch of the celiac artery 11, superior mesenteric artery 12, inferior mesenteric artery 13, internal iliac artery 16, external iliac artery 17, superior mesenteric vein 18, and/or inferior mesenteric vein 19. Alternatively, electrodes of the electrode set 21 may be placed on nerves 15 supplying the celiac artery 11, superior mesenteric artery 12, inferior mesenteric artery 13, internal iliac artery 16, external iliac artery 17, superior mesenteric vein 18, and/or inferior mesenteric vein 19. The number of electrodes in a set, as well as the number of electrode sets, employed for treatment of a particular condition may be influenced by factors such as, for example, the size of the electrodes, the prescribed stimulus amplitude, frequency, and/or pattern, and the size of the desired placement area.

Figure 6:
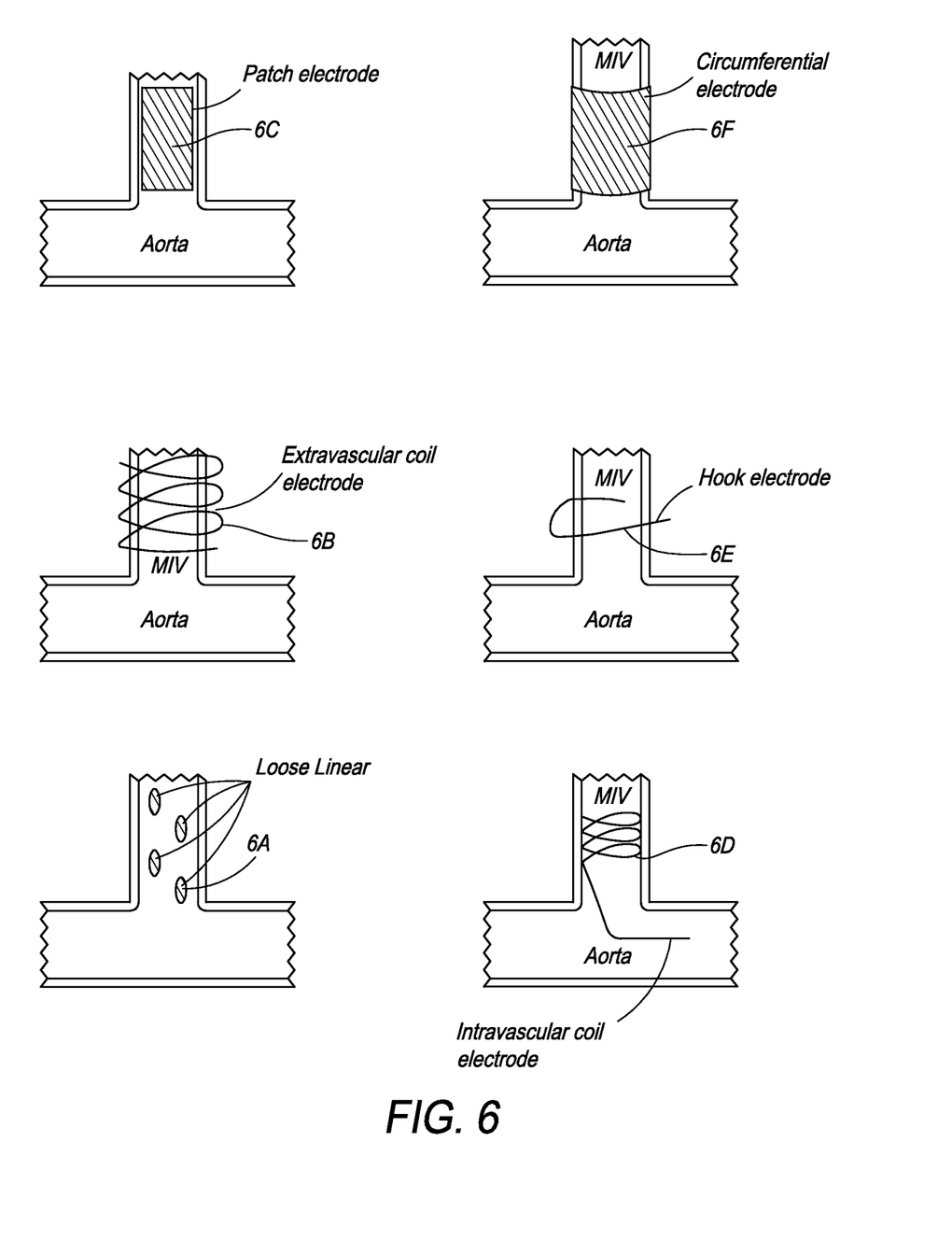
FIG. 6 illustrates exemplary forms and configurations of electrodes used in the methods disclosed herein.

FIG. 6 illustrates exemplary electrode designs, configurations, and arrangements including, for example, loose linear 6A, extravascular coil 6B, patch 6C, intravascular coil 6D, hook 6E, and circumferential 6F electrodes.

An electrical stimulus may be triggered by a transmitter external to the human body, similar to a remote transmitter for a cardiac pacemaker. With appropriate stimulus amplitude, frequency, and pattern, and appropriate treatment periods and duration, gastrointestinal diseases such as obesity can be treated without causing permanent injury to the surrounding tissue or organs.

Figure 5:
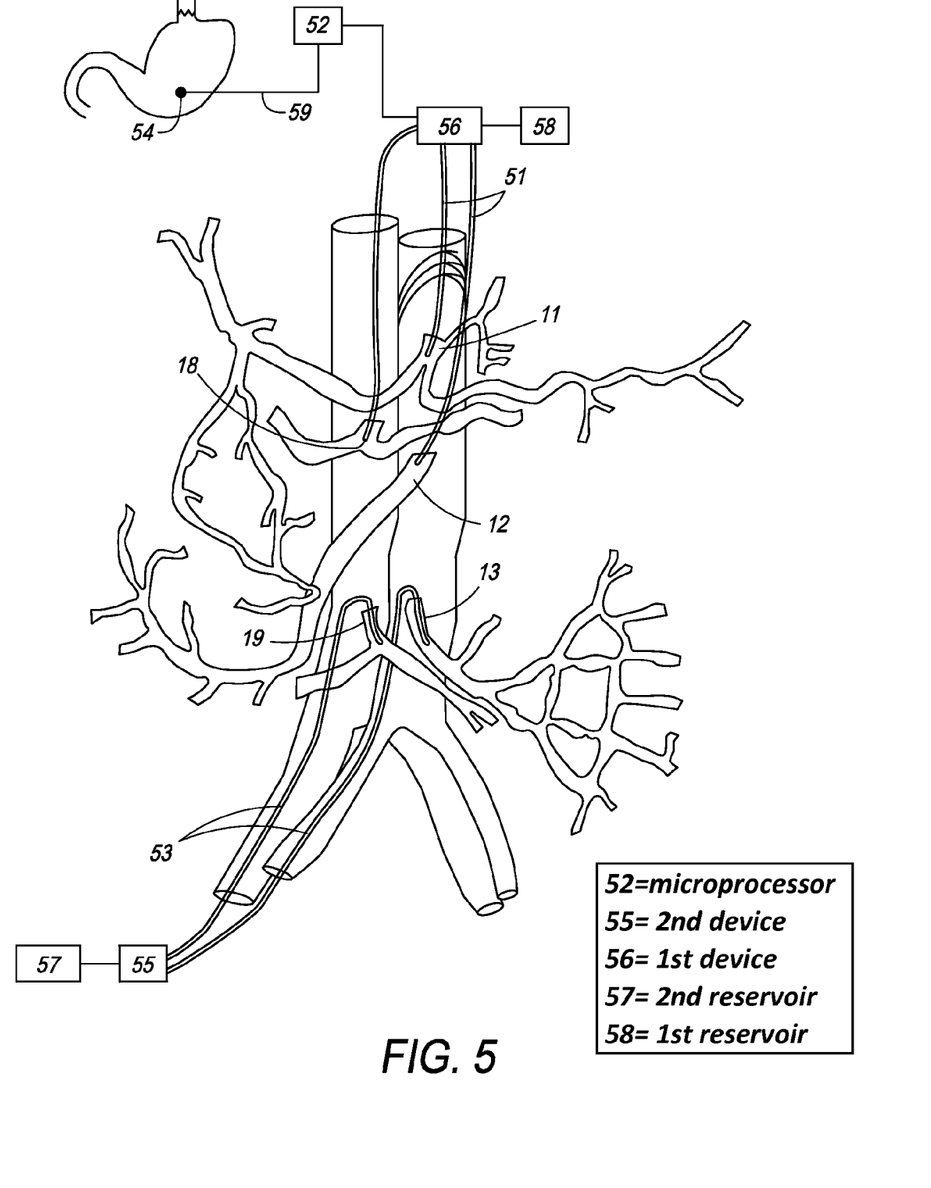
FIG. 5 is a schematic illustration of an exemplary infusion system implanted in the mesenteric circulation.

FIG. 5 shows another embodiment in which an infusion catheter 51 is placed in one or more of the celiac artery 11, superior mesenteric artery 12, or superior mesenteric vein 18 for delivery of a chemical stimulus rather than an electrical stimulus. A device comprising an infusion pump 56 is connected to a reservoir 58, which may supply a vasoactive or neuroactive chemical. The infusion catheter 51 can deliver a vasoactive or neuroactive chemical to one of the celiac artery 11, superior mesenteric artery 12, or superior mesenteric vein 18 or inferior mesenteric vein 19 to modify the blood flow to and/or from the gastrointestinal tract. This can result in gastrointestinal ischemia or congestion.

FIG. 5 also shows an embodiment in which an infusion catheter 53 is placed in one or more of the inferior mesenteric artery 13 or inferior mesenteric vein 19 for delivery of a chemical stimulus rather than an electrical stimulus. A device comprising an infusion pump 55 is connected to a reservoir 57, which may supply a vasoactive or neuroactive chemical. The infusion catheter 53 can deliver a vasoactive or neuroactive chemical to one of the inferior mesenteric artery 13 or inferior mesenteric vein 19 to modify the blood flow to and/or from the gastrointestinal tract. This can result in gastrointestinal ischemia or congestion.

A chemical stimulus "dose" can be provided continuously or intermittently. For example, a chemical stimulus may be provided one time, may be provided continuously for a prescribed period, or may be provided in a series of intermittent stimuli over a prescribed period. The prescribed period may be such as, for example, from about 0.1 µL/hr to about 1 L/min such as, for example, 0.1-10 µL/min. Intermittent chemical stimuli may be provided at regular, prescribed intervals within the treatment period. For example, intermittent chemical stimuli may be provided at a rate of 0.1 µL/min for 30 minutes. In other cases, intermittent chemical stimuli may be provided on an "as needed" basis. Also, certain treatments may include multiple chemical stimuli provided over any combination of varying treatment periods.

In some embodiments, a signal to deliver the vasoactive or neuroactive chemical may be triggered manually by, for example, a medical professional, a caregiver, or the subject. Alternatively, a set of sensing electrodes can detect one of the physiological parameters associated with a meal and generate a signal to cause the delivery of the chemical stimulus, which can affect blood supply to the gastrointestinal tract. However triggered, the signal to deliver the vasoactive or neuroactive chemical can regulate the volume, frequency, and/or pattern of vasoactive or neuroactive chemical delivered as well as the period and/or duration of the chemical stimulation. The prescribed chemical stimulus can curb a subject's appetite and/or induce anorexia, satiety, and/or weight loss in the subject.

A chemical stimulus may be triggered by a transmitter external to the human body, similar to a remote transmitter for a cardiac pacemaker. With appropriate dosing volume, frequency, and pattern, and appropriate treatment periods and duration, gastrointestinal diseases such as obesity can be treated without causing permanent injury to the surrounding tissue or organs.

Over time, stimulation, whether continuous or intermittent, whether electrical or chemical, may serve to tone the smooth muscle of the mesenteric vascular system. With sufficient tone, further stimulation may be reduced or eliminated. Thus, diseases of the gastrointestinal tract may be treated successfully using treatments of varying durations. For example, certain conditions may be treated successfully using a single treatment, while other conditions may require a more extended treatment such as, for example, one week, one month, six weeks, one year, or, in some cases, long term (including, e.g., life-long) treatment may be required.

Referring simultaneously to FIGS. 2 through 4, in some embodiments, the device 26, 36, 46, 56 may be controlled by a microprocessor 22, 32, 42, 52. In some embodiments, the microprocessor 22, 32, 42, 52 may be operably connected to the signal generator and may be programmed to control the length, power, and frequency of the electrical signals generated by the device 26, 36, 46, 56 over various treatments periods and/or durations. In other embodiments, the microprocessor 22, 32, 42, 52 may be operably connected to the pump and may be programmed to control the length, volume, and frequency of the chemical signals generated by the device 26, 36 46, 56 over varying treatments periods and/or durations.

In one exemplary embodiment, a subject can signal the ingestion of a meal using a remote control RF signaling device. Based on subject's desired weight loss, a microprocessor in the implanted signal generating device can send multiple trains of pulses after a preset time delay. In the case of, for example, a male subject for which a 150 pound weight loss is desired and a 1000 calorie daily diet is suggested, the preset time to start mesenteric vascular stimulation may be 10 minutes from the initiation of eating. A typical stimulation parameter can have a burst of, for example, 6 rectangular pulses of, for example, 2 msec duration and pulse amplitude of, for example, 10 mAmp. The duration of each single burst of 6 impulses may be, for example, 200 msec and have a frequency of, for example, 1 burst per second. The pulse trains may be interrupted by a quiescent phase of, for example, 800 msec. A quiescent phase may, for example, allow the mesenteric vascular musculature to repolarize. The pulse trains can induce contraction of, for example, the celiac and superior mesenteric artery, resulting in physiological obstruction to the flow of blood to the stomach and intestine, This can cause discomfort and/or pain, resulting in early satiety and/or loss of appetite in the subject.

The stimulation may continue until subject stops eating, after which the stimulation stops. Alternatively, sensors can be implanted in the gastrointestinal tract that sense ingestion of food and trigger the microprocessor which, in turn, triggers the signal generator to deliver stimulations to the celiac and superior mesenteric artery. The sensors also may detect the end of ingestion and transmit a shut off signal to the microprocessor which, in turn, will shut off the stimulator.

Based on a subject's continuing caloric restriction, the stimulation patterns can be adjusted by the subject's physician using an external remote controller without requiring additional surgery. Upon achieving desired weight loss, the stimulator can be remotely shut down and, if the subject starts gaining the weight back, the stimulator can be remotely turned on.

In certain embodiments, the methods described herein may be practiced using a neurostimulation system having at least one electrode set, at least one power source, and an extension connecting the power source to the electrode set. The electrode can be integrated into a lead, where the lead is a small conductor with more than one electrode integrated therein. In one embodiment, surgically implanted leads may be used including, for example, a 3587A RESUME II Lead, 3986 RESUME TL Lead, 3998 SPECIFY Lead, 3999 Hinged SPECIFY Lead, 3982 SYMMIX Lead, and/or 3987 On-Point PNS Lead (all from Medtronic, INC., Minneapolis, Minn.), or any other quadripolar leads with plate electrodes capable of creating multiple stimulation combinations over a broad area of paresthesia.

In one embodiment, device 26, 36, 36', 46, 56 may be an implantable battery-powered neurostimulator with non-invasive programmability, such as, (for example, an ITREL 3, a SYNERGY, a SYNERGYPLUS$^+$, or a SYNERGYCOMPACT$^+$ (all from Medtronic, Inc., Minneapolis, Minn.). Alternatively, the device 26, 46', 55 comprises a radiofrequency (RF) system, which can include an implanted receiver that detects radio-frequency signals through the skin from an external power source or transmitter such as MATTRIX transmitters (Medtronic, Inc., Minneapolis, Minn.).

In another embodiment, the extension may be a small conductor that electrically connects the power source to the lead. Exemplary extensions include low profile, low impedance extensions and/or bifurcated, low profile, low impedance extensions.

As shown in FIGS. 2 through 4, the present invention can optionally include additional sensing electrodes 24, 34, 44, 54 that are placed in the gastrointestinal tract or proximate to nerves supplying the gastrointestinal tract or the vascular system. The sensing electrodes 24, 34, 44, 54 may be capable of sensing one or more physiological stimuli such as, for example, esophageal peristalsis, esophageal pH, esophageal impedence, esophageal pressure, esophageal electrical activity, lower esophageal sphincter (LES) pressure, LES electrical activity, gastric peristalsis, gastric electrical activity, gastric chemical activity, gastric hormonal activity, gastric temperature, gastric pressure, gastric impedence and gastric pH, duodenal peristalsis, duodenal electrical activity, duodenal chemical activity, duodenal hormonal activity, duodenal temperature, duodenal pressure, duodenal impedance and duodenal pH, blood chemical activity, blood hormonal activity, vagal or other gastrointestinal neural activity, salivary chemical activity, biliary pressure, biliary electrical activity, biliary chemical activity, pancreatic pressure, pancreatic electrical activity, pancreatic chemical activity, pancreatic sphincter pressure, pancreatic sphincter electrical activity, biliary sphincter pressure, or biliary sphincter electrical activity, mesenteric vascular pressure, mesenteric vascular flow, and/or mesenteric vascular chemical contents.

Upon sensing an appropriate physiological stimulus, the sensing electrodes 24, 34, 44, 54 can transmit a signal to the device 26, 36, 46, 56, via wire or lead 29, 39, 49, 59 and processor 22, 32, 42, 52. The device 26, 36, 46, 56 may then begin, maintain, modulate, or stop electrical stimulation signal sent to the electrode set 21. Thus, the methods described herein can be more responsive to a subject's particular biological state and precisely modulate at least a portion of the mesenteric vasculature so that a part or the whole of the mesenteric system can contract or relax, thereby regulating the flow of blood into the gastrointestinal tract. Controlling the flow of blood into the gastrointestinal tract can also be achieved by turning off the transmitter of the external pacer. The stimulating electrode set 21 can be used in combination with additional pacing electrodes, as are known in the art, to treat disorders of gastrointestinal motility or function. It should be appreciated that the sensing electrodes can be implemented in any of the embodiments of this invention, including those depicted in FIGS. 3-5.

Any of the stimulating or sensing electrode sets can be placed by conventional surgical, laproscopic, endoscopic, radiological, or other minimally invasive vascular and surgical techniques to place the desired device or devices on or adjacent to or in communication with the structure with which it is to be associated. Conventional electrode stimulation devices may be used to practice the methods described herein.

It should be appreciated that where a cardiovascular condition, such as angina, is being treated, periods of stimulation may last much longer than in treating conditions related to inducing satiety or curbing a subject's appetite. In one embodiment, the treatment of angina would be effectuated by stimulating both the celiac and SMA arteries, as described above, concurrently for a period of several hours, such as 2, 3, 4, 5, 6, or more, after a meal.

The present invention is illustrated by the following examples. It is to be understood that the particular examples, materials, amounts, and procedures are to be interpreted broadly in accordance with the scope and spirit of the invention as set forth herein.

EXAMPLE 1

A mesenteric electrical stimulator is laparoscopically implanted into an adult male subject. The stimulator leads are implanted on the external surface of the celiac and superior mesenteric artery and the microcontroller is implanted in a pocket in the anterior abdominal wall.

Using remote control signals, the microcontroller sends multiple bursts of 10 rectangular pulses after a preset time delay of 10 minutes from the beginning of the meal. The microcontroller sends electrical stimuli having a pulse amplitude of 10 mAmp and a burst frequency of 2 bursts per second. The pulse trains are interrupted by a quiescent phase of 500 milliseconds (msec). The stimulation is carried out until patient stops eating after which the stimulation stops.

EXAMPLE 2

In acute experiments, mesenteric vascular stimulation is implanted into the mesenteric vasculature of a pig. The stimulator leads are implanted on the external surface of the celiac and superior mesenteric artery and is controlled by an external microcontroller. A typical stimulation parameter can have a burst of 10 pulses with a pulse amplitude of 20 mAmp and a burst frequency of 0.5 bursts per second. The duration of each bursts of 10 pulses is 400 msec with quiescent phase of 1600 msec to allow for repolarization of the mesenteric vascular muscle. The pulse trains will induce contraction of the celiac and superior mesenteric artery resulting in physiological obstruction to the flow of blood to the stomach and intestine. The decrease in the blood flow can be measured using a Doppler flow meter.

EXAMPLE 3

For chronic survival experiments, the stimulator is implanted into the mesenteric vasculature of the pig. The stimulator leads are implanted on the external surface of the celiac and superior mesenteric artery and the microcontroller is implanted in a pocket in the anterior abdominal wall or worn on a jacket or belt. A typical stimulation parameter can have a burst of 10 pulses with a pulse amplitude of 10 mAmp, duration of 400 msec and a burst frequency of 0.5 bursts per second. The burst trains are interrupted by a quiescent phase of 1600 msec to allow for repolarization of the mesenteric vascular muscle. The stimulator is turned on and off randomly and the food intake during on periods is compared to off period documenting lower food and calorie intake when the stimulator is on. In addition stimulator can be turned on continuously. The animal is allowed to free feed. Serial weight measures shows less weight gain or weight loss compared to free fed animals that do not have the stimulator turned on.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of treating a cardiovascular condition in a subject, the method comprising:
providing an apparatus comprising at least one electrode operably connected to a stimulus generator;
placing the at least one electrode in direct contact with a portion of a celiac artery or a portion of a branch of a celiac artery in order to electrically stimulate the celiac artery or the branch of a celiac artery; and
causing the stimulus generator to generate an electrical stimulus administered to the portion of the celiac artery or the portion of the branch of a celiac artery through the at least one electrode, wherein the electrical stimulus is effective to alter a flow of blood into the subject's gastrointestinal tract.

2. The method of claim 1 further comprising the steps of:
providing a second electrode operably connected to a stimulus generator;
placing the second electrode in electrical communication with a target comprising one or more of the following: an artery, other than the celiac artery or a branch of a celiac artery, of the gastrointestinal vasculature of the subject, a vein of the gastrointestinal vasculature of the subject, a nerve supplying an artery of the gastrointestinal vasculature of the subject, and a nerve supplying a vein of the gastrointestinal vasculature of the subject; and
causing the stimulus generator to generate an electrical stimulus administered to the target through the second electrode, wherein the electrical stimulus is effective for treating the cardiovascular condition.

3. The method of claim 1 wherein the cardiovascular condition comprises one of heart-failure, hypertension or angina.

4. The method of claim 2 wherein the target comprises an artery of the gastrointestinal vasculature or a nerve supplying an artery of the gastrointestinal vasculature of the subject and the electrical stimulus induces a contraction in the celiac artery or the branch of a celiac artery.

5. The method of claim 2 wherein the target comprises a vein or a nerve supplying a vein of the gastrointestinal vasculature of the subject and the electrical stimulus induces a contraction in the the celiac artery or the portion of the branch of a celiac artery.

6. The method of claim 2 wherein the apparatus further comprises a microprocessor operably connected to the stimulus generator, wherein at least one parameter of the stimulus is controlled by the microprocessor, wherein the parameter is selected from the group consisting of: the amplitude, frequency, pattern, period, and duration of the stimulation, and wherein causing the stimulus generator to generate an electrical stimulus administered to the target through one of the at least two electrodes comprises the microprocessor sending a signal to the stimulus generator signaling the stimulus generator to generate a stimulus.

7. The method of claim 1 wherein the apparatus further comprises at least one sensing electrode operably connected to the signal generator and in communication with at least a portion of the subject's gastrointestinal tract, wherein the at least one sensing electrode senses at least one physiological stimulus resulting from the subject feeling hungry or ingesting food, and wherein the at least one sensing electrode transmits a signal to the signal generator to administer an electrical signal to the target after sensing the at least one physiological stimulus resulting from the subject ingesting food.

8. A method of treating a cardiovascular condition in a subject, the method comprising:
providing an apparatus comprising at least two electrodes operably connected to a stimulus generator;
placing a first of the at least two electrodes in direct physical contact with a first target comprising a portion of a celiac artery or a portion of a branch of a celiac artery of the gastrointestinal vasculature of the subject;
placing a second of the at least two electrodes in electrical communication with a second target comprising one or more of the following: an artery of the gastrointestinal vasculature of the subject, a vein of the gastrointestinal vasculature of the subject, a nerve supplying an artery of the gastrointestinal vasculature of the subject, and a nerve supplying a vein of the gastrointestinal vasculature of the subject; and
causing the stimulus generator to generate an electrical stimulus administered to the first and second target through the at least two electrodes, wherein the electrical stimulus is effective to change a flow of blood into the subject's gastrointestinal tract through the portion of a celiac artery or the portion of a branch of a celiac artery.

9. The method of claim 8 wherein the cardiovascular condition comprises one of heart-failure, hypertension or angina.

10. The method of claim 8 wherein the second target comprises a superior mesenteric artery or a branch of a superior mesenteric artery of the gastrointestinal vasculature of the subject and the electrical stimulus induces a contraction in the the celiac artery or the portion of the branch of a celiac artery.

11. The method of claim 8 wherein the second target comprises an artery of the gastrointestinal vasculature of the subject and the electrical stimulus induces a contraction in the tone the celiac artery or the portion of the branch of a celiac artery.

12. The method of claim 8 wherein the apparatus further comprises a microprocessor operably connected to the stimulus generator, wherein at least one parameter of the stimulus is controlled by the microprocessor, wherein the parameter is selected from the group consisting of: the amplitude, frequency, pattern, period, and duration of the stimulation, and wherein causing the stimulus generator to generate an electrical stimulus administered to the first and second targets through the at least two electrodes comprises the microprocessor sending a signal to the stimulus generator signaling the stimulus generator to generate a stimulus.

13. The method of claim 8 wherein the apparatus further comprises at least one sensing electrode operably connected to the signal generator and in communication with at least a portion of the subject's gastrointestinal tract, wherein the at least one sensing electrode senses at least one physiological stimulus resulting from the subject feeling hungry or ingesting food, and wherein the at least one sensing electrode transmits a signal to the signal generator to administer an electrical signal to the target after sensing the at least one physiological stimulus resulting from the subject ingesting food.

14. A method of treating a cardiovascular condition in a subject, the method comprising:
providing a stimulus generator;
providing at least two electrodes which are configured to operably connect to said stimulus generator;
instructing a person to place a first of the at least two electrodes in direct physical contact with a first target in the subject, said first target comprising a portion of a celiac artery or a portion of a branch of a celiac artery of the gastrointestinal vasculature of the subject,
instructing a person to place a second of the at least two electrodes in electrical communication with a second target in the subject, said second target comprising one or more of the following: an artery of the gastrointestinal vasculature of the subject, a vein of the gastrointestinal vasculature of the subject, a nerve supplying an artery of the gastrointestinal vasculature of the subject, and a nerve supplying a vein of the gastrointestinal vasculature of the subject; and instructing a person to cause the stimulus generator to generate an electrical stimulus administered to the first and second target through the at least two electrodes, wherein the electrical stimulus is effective to change a flow of blood into the subject's gastrointestinal tract through the portion of a celiac artery or the portion of a branch of a celiac artery.

* * * * *